(12) United States Patent
Ellis

(10) Patent No.: US 9,132,295 B2
(45) Date of Patent: Sep. 15, 2015

(54) COMPOSITION HAVING STABILIZED PERFLUOROCARBONS

(71) Applicant: Indermica, Inc., Mill Valley, CA (US)

(72) Inventor: Jennifer Clara Ellis, Lawton, OK (US)

(73) Assignee: Indermica, Inc., Greenbrae, CA (US)

(*) Notice: Subject to any disclaimer, the term of this patent is extended or adjusted under 35 U.S.C. 154(b) by 61 days.

(21) Appl. No.: 13/975,110

(22) Filed: Aug. 23, 2013

(65) Prior Publication Data

US 2015/0057372 A1 Feb. 26, 2015

(51) Int. Cl.
| | |
|---|---|
| *A61K 47/00* | (2006.01) |
| *A61K 47/06* | (2006.01) |
| *A61Q 19/08* | (2006.01) |
| *A61K 8/06* | (2006.01) |
| *A61K 8/70* | (2006.01) |
| *A61K 8/81* | (2006.01) |

(52) U.S. Cl.
CPC ............... *A61Q 19/08* (2013.01); *A61K 8/062* (2013.01); *A61K 8/70* (2013.01); *A61K 8/8152* (2013.01)

(58) Field of Classification Search
CPC ....... A61K 8/062; A61K 8/70; A61K 8/8152; A61Q 19/08
USPC .................................................. 514/672, 777
See application file for complete search history.

(56) References Cited

U.S. PATENT DOCUMENTS

| | | | |
|---|---|---|---|
| 6,649,145 B2 | 11/2003 | McGrath et al. | |
| 8,343,515 B2 | 1/2013 | Huvard et al. | |
| 2013/0045290 A1* | 2/2013 | Somerville et al. | 424/774 |
| 2013/0177505 A1* | 7/2013 | Somerville et al. | 424/47 |
| 2014/0271524 A1* | 9/2014 | Claiborne et al. | 424/78.03 |

FOREIGN PATENT DOCUMENTS

EP   1064989 A1 *  1/2001   .............. B01F 17/00

* cited by examiner

*Primary Examiner* — My-Chau T Tran
(74) *Attorney, Agent, or Firm* — Lee & Hayes, PLLC

(57) ABSTRACT

An emulsion having stabilized perfluorocarbon(s) that includes an aqueous solution, an oil solution and a third phase which includes at least one perfluorocarbon and methods of making the stable perfluorocarbon containing emulsions. The aqueous and oil phases are first mixed together to form the emulsion. At least one perfluorocarbon is then added to the emulsion. Either the aqueous based solution or oil based solution may include at least one thickener. Moreover, the perfluorocarbon containing emulsion remains stable for a period of at least two weeks.

20 Claims, 1 Drawing Sheet

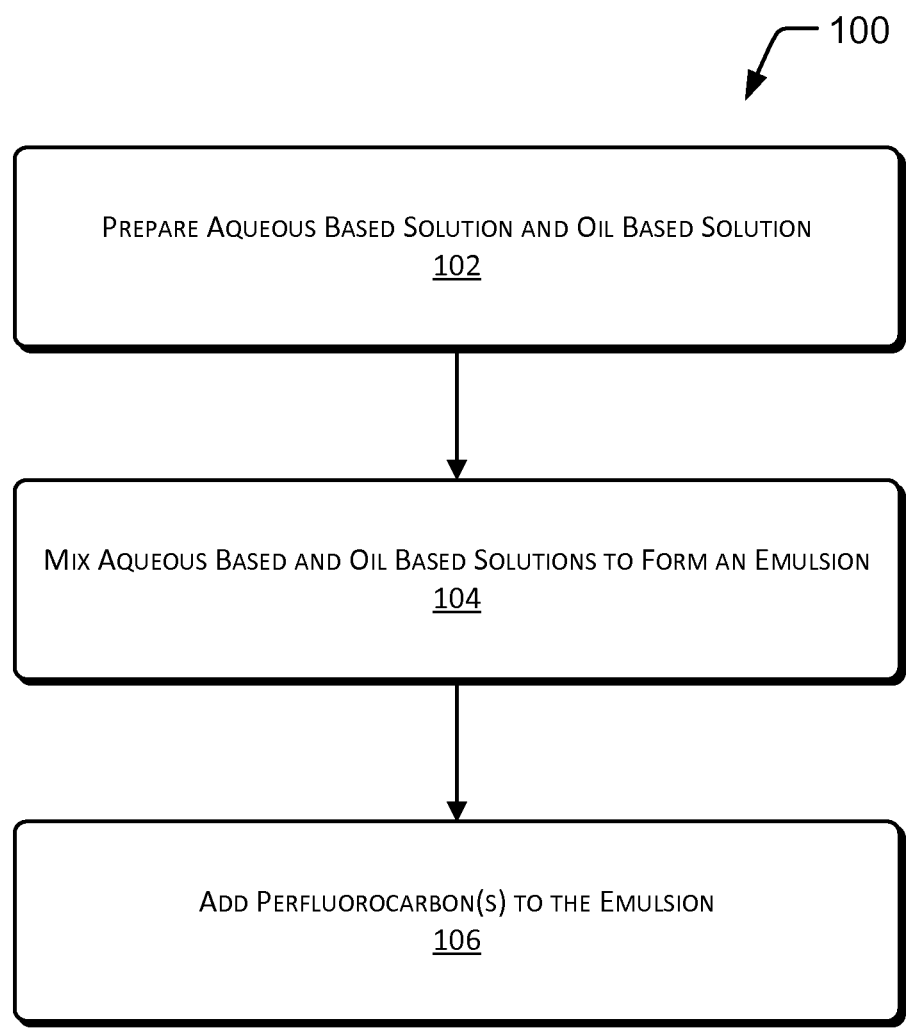

COMPOSITION HAVING STABILIZED PERFLUOROCARBONS

BACKGROUND

Changes in skin appearance which result as a person ages can be due to many factors, such as, for example, changes in elastin and collagen levels in the skin. Skin appearance can also be affected by uneven pigment and changes in skin thickness, such as the thinning of the skin under and around the eyes. External or environmental factors, such as sun, weather, pollution, etc. also play a major role in skin appearance. Moreover, as life expectancies continue to rise and people continue to live longer, there is a continued increase in the demand for treatments which improve the appearance of skin and reverse the effects of aging. As the demand for such treatments continue to increase, the skin care and cosmetic market also continues to grow. However, there remains the need for improvement in treatments and compositions which improve skin appearance by, for example, reducing wrinkles and other symptoms associated with aging.

Perfluorocarbons are compounds that are capable of dissolving large volumes of gases, such as oxygen. Such compounds are known to be chemically and biologically inert, but are capable of transporting diffused gases across distances. Moreover, the ability to dissolve large volumes of gases has led to the increased use of perfluorocarbons in medical and cosmetic compositions, such as anti-wrinkle and anti-aging compositions. However, such perfluorocarbons are neither water soluble nor oil soluble and have shown to be unstable when added to medical and cosmetic compositions, such as emulsions.

BRIEF SUMMARY

This summary is provided to introduce simplified concepts of compositions having stabilized perfluorocarbons and methods for preparing such compositions. Additional details of example methods and compositions are further described below in the Detailed Description. The embodiments described herein are not mutually exclusive and aspects of the various embodiments may be combined to arrive at other embodiments within the scope of the claims. This summary is not intended to identify essential features of the claimed subject matter, nor is it intended for use alone in determining the scope of the claimed subject matter.

According to an embodiment, the present invention concerns a method for preparing a composition that stably includes at least one perfluorocarbon. The method includes preparing an aqueous based solution; preparing an oil based solution; contacting the aqueous based solution and the oil based solution to form an emulsion; and contacting the emulsion with at least one perfluorocarbon to thereby form a perfluorcarbon containing emulsion that is stable for at least two weeks. Moreover, either the aqueous based solution or oil based solution may include at least one thickener.

Another embodiment concerns an emulsion that stably contains at least one perfluorocarbon which includes a first phase comprising an aqueous based solution, a second phase comprising an oil based solution and a third phase comprising at least one perfluorocarbon wherein the at least one perfluorocarbon is stable in the emulsion for a period of at least two weeks. Moreover, either the aqueous based solution or oil based solution may include at least one thickener.

Another embodiment concerns a method for treating wrinkled skin which includes contacting an area of skin in need of treatment with an emulsion according to the present disclosure.

Yet another embodiment concerns an anti-wrinkle composition which includes the emulsion according to the present disclosure.

BRIEF DESCRIPTION OF THE DRAWING

The detailed description is set forth with reference to the accompanying FIGURE.

FIG. 1 is a flow diagram of an embodiment of an example method for preparing a composition that stably contains at least one perfluorocarbon.

DETAILED DESCRIPTION

The present disclosure relates to compositions which stably include at least one perfluorocarbon and methods of preparing such compositions. The compositions may be used on skin (e.g. the skin of a subject in need of such treatment) to reduce wrinkles and fine lines and improve the overall appearance of skin. According to an embodiment, the composition is in the form of an emulsion and may be used as an anti-wrinkle and/or anti-aging composition. Emulsions are a common form for cosmetic and medical products for delivery of active ingredients. Moreover, an emulsion is generally a mixture of two or more normally immiscible liquids in which one is dispersed in the other as microscopic or ultramicroscopic droplets. Emulsions may be, for example, oil-in-water (o/w), water-in-oil (w/o), or a microemulsion (e.g. an emulsion within an emulsion).

According to an embodiment, the invention concerns a method for preparing a stable perfluorocarbon containing composition. Moreover, the method includes preparing an aqueous based solution; preparing an oil based solution; contacting the aqueous based solution and the oil based solution to form an emulsion; and contacting the emulsion with at least one perfluorocarbon to thereby form a perfluorocarbon containing emulsion. According to certain embodiments, either the aqueous based solution or the oil based solution may include at least one thickener. The present invention enables the perfluorocarbon containing emulsion to be prepared such that the perfluorocarbon stably remains in the emulsion. According to another embodiment, the emulsion, prior to adding the perfluorocarbon, may be mixed with another aqueous based solution or oil based solution to form a second emulsion or microemulsion.

According to certain embodiments, the perfluorocarbon may be perfluorohexane, perfluoroperhydrophenanthrene, perfluorodecalin, perfluorodimethylcyclohexane, pentafluoropropane or any combination thereof. In certain embodiments, the perfluorocarbon may include perfluorohexane; perfluoroperhydrophenanthrene; perfluorodecalin; and perfluorodimethylcyclohexane. Perfluorocarbons are products that are fully fluorinated perfluorocarbons having a capacity to carry gases, such as oxygen (e.g., $O_2$), nitrogen (e.g., $N_2$) and carbon dioxide (e.g., $CO_2$). Perfluorocarbons are inert materials and are not oil soluble or water-soluble and thus create a third phase in emulsions. While perfluorocarbons contain air, they can be enriched with other gases such as oxygen. Typical compositions of the disclosure contain from about 1% to about 20% by weight, from about 3% to about 15% by weight, or from about 4% to about 10% by weight, of the perfluorocarbon. Lower concentrations may be employed in cosmetic or medical compositions for less pronounced conditions (e.g. situations where there skin has fewer and/or shallower wrinkle) and higher concentrations may be employed with more acute conditions.

According to certain embodiments, the thickener may be a carbomer thickener, such as Carbopol® Ultrez 10, Carbopol® Ultrez 30, or Carbopol® Polymer 980, or an acrylates/C10-30 alkyl acrylate crosspolymer thickener, such as, for example, Carbopol® Ultrez 20, Carbopol® Ultrez 21, or Carbopol® Polymer ETD 2020. Typical compositions of the disclosure contain from about 0.1% to about 10% by weight, from about 1% to about 8% by weight, or from about 2% to about 4% by weight of thickener. According to certain embodiments, the compositions may contain less than 10%, less than 9%, less than 8%, less than 7%, less than 6%, less than 5%, less than 4%, less than 3%, less than 2%, less than 1%, or less than 0.5% by weight.

The perfluorcarbons may stably remain in the composition for at least two weeks; at least one month; at least two months, at least three months, at least four months, at least five months or at least six months. By "stably remain in the composition" is meant that the at least one perfluorocarbon remains in the composition without any appreciable dissipation of the at least one perfluorocarbon. Moreover, dissipation of the at least one perfluorocarbon can be detected by, for example, the appearance of a foamy layer at the top of the composition.

FIG. 1 is a flow diagram of an embodiment of an example method 100 for preparing a composition that stably contains at least one perfluorocarbon. At 102, the method 100 includes preparing an aqueous based solution and an oil based solution. According to certain embodiments the aqueous based solution may be between 30 wt. % to about 70 wt. % of the final emulsion and may be, for example, water, deionized water, saline, or sterilized water in which water soluble active agents and other ingredients are diluted, dispersed or suspended. Moreover, according to certain embodiments, the oil based solution may be between 30 wt. % to about 70 wt. % of the final emulsion and may be, for example, sunflower seed oil, safflower oil, mineral oil, or any cosmetically or pharmaceutically acceptable oil, in which oil soluble active agents and other ingredients are diluted, dispersed or suspended. Either the aqueous based solution or the oil based solution may also include at least one thickener.

At 104, the method 100 includes mixing or contacting the aqueous based solution and oil based solution to form an emulsion. According to an embodiment, the emulsion may be formed by, for example, vigorously mixing one of the aqueous based solution or oil based solution into the other. For example, in the case of an oil-in-water emulsion, the aqueous based solution is vigorously stirred or shaken while the oil based solution is added. Alternatively, the two solutions can be added together and then heated and mixed. Yet another method involves combining the two solutions together to form a mixture of the two solutions and then exposing the mixture to high shear forces until the emulsion forms. In still other embodiments, the emulsion can be in the form of a microemulsion wherein a first emulsion is formed and then the first emulsion is mixed with an additional aqueous based solution or oil based solution to form a second emulsion. For example, an aqueous based solution containing water soluble ingredients is mixed with an oil based solution containing oil soluble ingredients to form a first emulsion. This first emulsion may then be mixed with a second oil based solution or aqueous based solution to form a second emulsion or microemulsion.

According to certain embodiments, additional ingredients such as surfactants, acids, and emulsifiers may be added to one or both of the solutions, prior to forming the emulsion, to help stabilize the emulsion. According to certain embodiments, additional active ingredients may also be added after the emulsion has formed and prior to the addition of the perfluorocarbon. For example, during embodiments wherein the aqueous and oil based solutions are mixed at an elevated temperature, temperature sensitive active ingredients may be added after the emulsion has cooled, for example, to room temperature.

At 106, after the emulsion has formed, the method 100 includes adding at least one perfluorocarbon to the emulsion. According to an embodiment, the perfluorocarbon(s) may be added, for example, by pouring or pumping the one or more perfluorocarbon(s) into the emulsion while slowly stirring or agitating the emulsion. The final perfluorocarbon containing emulsion may be in the form of, for example, a lotion, gel, or cream.

According to other embodiments, after the perfluorocarbon has been added to the emulsion, additional ingredients such as, for example, pH modifiers, chelators, and perfumes may be added.

After the perfluorocarbon containing emulsion is produced, the emulsion may be stored in an air tight-container. Examples of suitable air-tight containers include airless containers that can be vacuum sealed, such as airless pumps or airless jars. According to certain embodiments, the airless container may be filled from its bottom with the perfluorocarbon containing emulsion after which the bottom is sealed such that the container is airtight. In other embodiments, an amount of nitrogen gas is sprayed into the filled container just before the container is sealed to replace any residual air in the container with the nitrogen.

Generally in the practice of methods of treating skin, a therapeutically effective amount of the composition is topically applied to the skin of a subject in need of anti-wrinkle or anti-aging treatment in a predetermined or as-needed regimen either at intervals by application of the composition or the like, it generally being the case that gradual anti-wrinkle and/or anti-aging is noted with each successive application.

"Therapeutically effective amount" or "effective amount" refers to the amount of a compound that, when administered to a subject for treating a disease, or at least one of the clinical symptoms of a disease or disorder, is sufficient to affect such treatment for the disease, disorder, or symptom. The "therapeutically effective amount" can vary depending on the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be readily apparent to those skilled in the art or capable of determination by routine experimentation.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, or inhibiting at least one physical parameter which may not be discernible to the subject. Further, "treating" or "treatment" refers to delaying or preventing the onset or reoccurrence of the disease or disorder or at least symptoms thereof in a subject which may be exposed to or predisposed to or may have previously suffered from a disease or disorder even though that subject does not yet experience or display symptoms of the disease or disorder.

It should be understood that the ingredients particularly mentioned above are merely examples and that some embodiments of formulations that include the compositions of the present invention may have other suitable components and agents. The compositions of the invention may be used for, among other things, pharmaceutical and cosmetic purposes and may be formulated with different ingredients according to the desired use.

EXAMPLES

Certain embodiments of the present invention are illustrated by the following Examples. The present invention may, however, be embodied in many different forms and should not be construed as limited to the embodiments set forth herein; rather, these embodiments are provided so that this disclosure will be thorough and complete, and will fully convey the scope of the invention to those skilled in the art. Moreover, unless otherwise specified, all percentages given are by weight.

The following examples concern anti-wrinkle compositions. Example 1 exemplifies an anti-wrinkle composition made according to an embodiment of the present invention. Embodiment 2 concerns an anti-wrinkle composition that shows the perfluorcarbon being added after the emulsion is formed but without the use of an appropriate thickener in either the aqueous based or oil based solutions. Examples 3 and 4 show anti-wrinkle composition where the perfluorcarbon is added in either the aqueous phase of the oily phase before the two phases are combined to form the emulsion. Examples 4 and 5 show anti-wrinkle composition that employ an appropriate thickener but where the perfluorcarbon is added in either the aqueous phase or the oily phase.

Example 1

| Part A | |
|---|---|
| WATER | 45.3% |
| GLYCERIN | 1.0% |
| BUTYLENE GLYCOL | 5.0% |
| *ALOE VERA* CONCENTRATE | 0.1% |
| Part B | |
| CARBOPOL ULTREZ 20 | 0.3% |
| Part C | |
| FINSOLV TN | 6.0% |
| LIPONATE GC | 3.0% |
| ABILEM 90 | 1.0% |
| GLYCERYL STEARATE GMS-450 | 4.5% |
| CETYL ALCOHOL (LANETTE) | 2.5% |
| STEARIC ACID (EMERSOL 132NF) | 3.0% |
| ISOPROPYL PALMITATE | 5.0% |
| HYALURONIC ACID | 0.5% |
| Part D | |
| PHYTOCELL TEC SOLAR *VITIS* GRAPE | 0.5% |
| PHYTOCELL TEC ALP ROSE | 0.5% |
| OPTIPHEN | 1.0% |
| PHYTOCELL TEC *MALUS DOMESTICA* | 0.5% |
| ARGIRELINE | 5.0% |
| LEUPHASYL | 5.0% |
| Part E | |
| FI FLOW BTX (perfluorohexane; perfluoroperhydrophenanthrene; perfluorodecalin; and perfluorodimethylcyclohexane) | 10.0% |
| Part F | |
| PROCOL LA-4 (LAURETH 4) | 0.2% |
| TRIETHANOLAMINE 99% | QS [1] |
| PERFUME GREEN TEA IV N04038 AI | 0.1% |

[1] QS = Quantity Sufficient to raise pH of composition to about 6.0-6.5

Part A and Part B were mixed together at a temperature of between 80-85° C. until uniform to form an aqueous phase. Part C, which is an oily phase solution, was then added and the combination was mixed well until an emulsion was formed. The emulsion was then allowed to cool to between 25-30° C. after which Part D was added and mixed until the emulsion was smooth. Part E, which includes a mixture of perfluorocarbons, was then added until uniformly incorporated into the emulsion after which Part F was added to adjust the pH to 6.0-6.5. The resulting perfluorocarbon containing emulsion was then stored in an air-tight container. Moreover, the perfluorocarbons remained stable in the emulsion for at least six months.

Example 2

| Part A | |
|---|---|
| Water | 25.0% |
| Carbopol 940 Sln | 20.0% |
| Glycerin | 1.0% |
| Butylene Glycol | 5.0% |
| *Aloe vera* concentrate | 0.1% |
| Part B | |
| Finsolv TN | 6.0% |
| Liponate GC | 3.0% |
| Abilem 90 | 1.0% |
| Glyceryl Stearate | 4.5% |
| Cetyl Alcohol | 2.5% |
| Stearic Acid | 3.0% |
| IPP | 5.0% |
| Hyaluronic Acid | 0.5% |
| Part C | |
| Phytocell Solar *Vitis* Grape | 0.5% |
| Phytocell Alp Rose | 0.5% |
| Optiphen | 1.0% |
| Phytocell *Malus Domestica* | 0.5% |
| Argireline | 5.0% |
| Leuphasyl | 5.0% |
| Part D | |
| FiFlow BTX | 10.0% |

Part A and Part B were mixed well until an emulsion was formed at a temperature of between 80-85° C. The emulsion was then allowed to cool to between 25-30° C. after which Part C was added and mixed until the emulsion was smooth. Part D was then added until uniformly incorporated into the emulsion. The resulting perfluorocarbon containing emulsion was then stored in an air-tight container. However, the perfluorocarbons immediately dissipated out of the emulsion and the oily phase and aqueous phase separated and curdled.

Example 3

| Part A | |
|---|---|
| Water | 25.0% |
| Carbopol 940 Sln | 20.0% |
| Glycerin | 1.0% |
| Butylene Glycol | 5.0% |
| *Aloe vera* concentrate | 0.1% |

| Part B | |
|---|---|
| Finsolv TN | 6.0% |
| Liponate GC | 3.0% |
| Abilem 90 | 1.0% |
| Glyceryl Stearate | 4.5% |
| Cetyl Alcohol | 2.5% |
| Stearic Acid | 3.0% |
| IPP | 5.0% |
| Hyaluronic Acid | 0.5% |
| FiFlow BTX | 10.0% |

| Part C | |
|---|---|
| Phytocell Solar *Vitis* Grape | 0.5% |
| Phytocell Alp Rose | 0.5% |
| Optiphen | 1.0% |
| Phytocell *Malus Domestica* | 0.5% |
| Argireline | 5.0% |
| Leuphasyl | 5.0% |

Part A and Part B were mixed well until an emulsion was formed at a temperature of between 80-85° C. The emulsion was then allowed to cool to between 25-30° C. after which Part C was then added until uniformly incorporated into the emulsion. The resulting perfluorocarbon containing emulsion was then stored in an air-tight container. However, the perfluorocarbons immediately dissipated out of the emulsion and the oily phase and aqueous phase separated and curdled.

Example 4

| Part A | |
|---|---|
| Water | 25.0% |
| Carbopol 940 Sln | 20.0% |
| Glycerin | 1.0% |
| Butylene Glycol | 5.0% |
| *Aloe vera* concentrate | 0.1% |
| FiFlow BTX | 10.0% |

| Part B | |
|---|---|
| Finsolv TN | 6.0% |
| Liponate GC | 3.0% |
| Abilem 90 | 1.0% |
| Glyceryl Stearate | 4.5% |
| Cetyl Alcohol | 2.5% |
| Stearic Acid | 3.0% |
| IPP | 5.0% |
| Hyaluronic Acid | 0.5% |

| Part C | |
|---|---|
| Phytocell Solar *Vitis* Grape | 0.5% |
| Phytocell Alp Rose | 0.5% |
| Optiphen | 1.0% |
| Phytocell *Malus Domestica* | 0.5% |
| Argireline | 5.0% |
| Leuphasyl | 5.0% |

Part A and Part B were mixed well until an emulsion was formed at a temperature of between 80-85° C. The emulsion was then allowed to cool to between 25-30° C. after which Part C was then added until uniformly incorporated into the emulsion. The resulting perfluorocarbon containing emulsion was then stored in an air-tight container. However, the perfluorocarbons immediately dissipated out of the emulsion and the oily phase and aqueous phase separated and curdled.

Example 5

| Part A | |
|---|---|
| Water | 45.6% |
| Carbopol Ultrez 20 | 0.3% |
| Glycerin | 1.0% |
| Butylene Glycol | 5.0% |
| *Aloe vera* concentrate | 0.1% |
| FiFlow BTX | 10.0% |

| Part B | |
|---|---|
| Finsolv TN | 6.0% |
| Liponate GC | 3.0% |
| Abilem 90 | 1.0% |
| Glyceryl Stearate | 4.5% |
| Cetyl Alcohol | 2.5% |
| Stearic Acid | 3.0% |
| IPP | 5.0% |
| Hyaluronic Acid | 0.5% |

| Part C | |
|---|---|
| Phytocell Solar *Vitis* Grape | 0.5% |
| Phytocell Alp Rose | 0.5% |
| Optiphen | 1.0% |
| Phytocell *Malus Domestica* | 0.5% |
| Argireline | 5.0% |
| Leuphasyl | 5.0% |

Part A and Part B were mixed well until an emulsion was formed at a temperature of between 80-85° C. The emulsion was then allowed to cool to between 25-30° C. after which Part C was then added until uniformly incorporated into the emulsion. The resulting perfluorocarbon containing emulsion was then stored in an air-tight container. However, the perfluorocarbons dissipated out of the emulsion within hours.

Example 6

| Part A | |
|---|---|
| Water | 45.6% |
| Carbopol Ultrez 20 | 0.3% |
| Glycerin | 1.0% |
| Butylene Glycol | 5.0% |
| *Aloe vera* concentrate | 0.1% |

| Part B | |
|---|---|
| Finsolv TN | 6.0% |
| Liponate GC | 3.0% |
| Abilem 90 | 1.0% |
| Glyceryl Stearate | 4.5% |
| Cetyl Alcohol | 2.5% |
| Stearic Acid | 3.0% |
| IPP | 5.0% |
| Hyaluonic Acid | 0.5% |
| FiFlow BTX | 10.0% |

| Part C | |
|---|---|
| Phytocell Solar *Vitis* Grape | 0.5% |
| Phytocell Alp Rose | 0.5% |
| Optiphen | 1.0% |
| Phytocell *Malus Domestica* | 0.5% |
| Argireline | 5.0% |
| Leuphasyl | 5.0% |

Part A and Part B were mixed well until an emulsion was formed at a temperature of between 80-85° C. The emulsion was then allowed to cool to between 25-30° C. after which Part C was then added until uniformly incorporated into the emulsion. The resulting perfluorocarbon containing emulsion was then stored in an air-tight container. However, the perfluorocarbons dissipated out of the emulsion within hours.

While applicant's disclosure has been provided with reference to specific embodiments above, it will be understood that modifications and alterations in the embodiments disclosed may be made by those practiced in the art without departing from the spirit and scope of the invention. All such modifications and alterations are intended to be covered.

I claim:

1. A method for preparing a stable perfluorocarbon containing composition, the method comprising:
   a. preparing an aqueous based solution;
   b. preparing an oil based solution;
   c. contacting the aqueous based solution and the oil based solution to form an emulsion; and
   d. contacting the emulsion with at least one perfluorocarbon to thereby form a perfluorocarbon containing composition that is stable for at least two weeks;
wherein the aqueous based solution, the oil based solution or both includes at least one thickener.

2. The method according to claim 1, wherein the at least one perfluorocarbon is stable in the composition for at least 1 month.

3. The method according to claim 2, wherein the at least one perfluorocarbon is stable in the composition for at least 6 months.

4. The method according to claim 1, wherein said perfluorocarbon is selected from the group consisting of perfluorohexane; perfluoroperhydrophenanthrene; perfluorodecalin; perfluorodimethylcyclohexane; pentafluoropropane; and mixtures thereof.

5. The method according to claim 4, wherein said perfluorocarbon includes perfluorohexane; perfluoroperhydrophenanthrene; perfluorodecalin; and perfluorodimethylcyclohexane.

6. The method according to claim 1, wherein said thickener includes a carbomer thickener, an acrylates/C10-30 alkyl acrylate crosspolymer thickener, or a combination thereof.

7. The method according to claim 1, wherein said composition includes from about 1 wt. % to about 20 wt. % of the perfluorocarbon.

8. The method according to claim 7, wherein said composition includes from about 3 wt. % to about 15 wt. % of the perfluorocarbon.

9. The method according to claim 8, wherein said composition includes from about 4 wt. % to about 10 wt. % of the perfluorocarbon.

10. An emulsion that stably contains at least one perfluorocarbon, the composition comprising a first phase comprising an aqueous based solution, a second phase comprising an oil based solution and a third phase comprising at least one perfluorocarbon,
    wherein the aqueous based solution, the oil based solution or both includes at least one thickener, and
    the at least one perfluorocarbon is stable in the emulsion for a period of at least two weeks.

11. The emulsion according to claim 10, wherein the at least one perfluorocarbon is stable in the emulsion for at least 1 month.

12. The emulsion according to claim 11, wherein the at least one perfluorocarbon is stable in the emulsion for at least 6 months.

13. The emulsion according to claim 10, wherein said perfluorocarbon is selected from the group consisting of perfluorohexane; perfluoroperhydrophenanthrene; perfluorodecalin; perfluorodimethylcyclohexane; pentafluoropropane; and mixtures thereof.

14. The emulsion according to claim 13, wherein said perfluorocarbon includes perfluorohexane; perfluoroperhydrophenanthrene; perfluorodecalin; and perfluorodimethylcyclohexane.

15. The emulsion according to claim 10, wherein said thickener includes a carbomer thickener, an acrylates/C10-30 alkyl acrylate crosspolymer thickener, or a combination thereof.

16. The emulsion according to claim 10, wherein said composition includes from about 1 wt. % to about 20 wt. % of the perfluorocarbon.

17. The emulsion according to claim 16, wherein said composition includes from about 3 wt. % to about 15 wt. % of the perfluorocarbon.

18. The emulsion according to claim 17, wherein said composition includes from about 4 wt. % to about 10 wt. % of the perfluorocarbon.

19. A method for treating wrinkled skin comprising contacting an area of skin in need of treatment with the emulsion according to claim 10.

20. An anti-wrinkle composition, comprising the emulsion according to claim 10.

* * * * *